United States Patent
Ahlquist et al.

[11] Patent Number: 5,804,439
[45] Date of Patent: Sep. 8, 1998

[54] PLASMID ENCODING HYBRID RNA VIRUS

[75] Inventors: Paul G. Ahlquist; Roy C. French, both of Madison; Robert F. Sacher, McFarland, all of Wis.

[73] Assignee: Mycogen Plant Science, Inc., San Diego, Calif.

[21] Appl. No.: 773,821

[22] Filed: Dec. 27, 1996

Related U.S. Application Data

[62] Division of Ser. No. 473,617, Jun. 7, 1995, Pat. No. 5,627,060, which is a division of Ser. No. 445,990, May 22, 1995, Pat. No. 5,602,242, which is a continuation of Ser. No. 158,082, Nov. 23, 1993, abandoned, which is a continuation of Ser. No. 978,313, Nov. 17, 1992, abandoned, which is a continuation of Ser. No. 518,242, May 4, 1990, abandoned, which is a continuation of Ser. No. 12,253, Feb. 9, 1987, abandoned.

[51] Int. Cl.$^6$ .............. C12N 7/01; C12N 15/33; C12N 15/79; C12N 15/83
[52] U.S. Cl. .............. 435/320.1; 424/199.1; 435/172.3; 536/23.72
[58] Field of Search .............. 435/69.1, 70.1, 435/91.3, 91.1, 172.1, 172.3, 235.1, 320.1; 536/23.72; 424/199.1, 205.1

[56] References Cited

U.S. PATENT DOCUMENTS 5,602,242  2/1997  Ahlquist et al. .............. 536/23.72

OTHER PUBLICATIONS

Ahlquist et al. (1984) J. Mol. Biol. 172:369–383.
Meshi et al. (1981) Mol. Gen. Genet. 184:20–25.
Stanway et al. (1986) J. Virol. 57:1187.
Semler et al. (1986) Proc. Natl. Acad. Sci. USA 83:1777.
Takamatsu et al. (1987) Embo J. 6:307–311.
French et al. (1986) Science 231:1294–1297.
Sleat et al. (1986) Virology 155:299–308.
Agol et al. (1984) Virology 136:41–55.
Habili et al. (1974) Virology 61(2):443–449.
Luria et al. (1978) General Virology, Third Edition, pp. 58–60.
Sacher et al. (1988) Virology 167:15–24.
Lojek et al. (1972) Canadian Journal of Microbiology 18:51–55.

*Primary Examiner*—George C. Elliott
*Assistant Examiner*—Thomas G. Larson
*Attorney, Agent, or Firm*—Saliwanchik, Lloyd & Saliwanchik

[57] ABSTRACT

A recombinant RNA virus is provided allowing encapsidation of genetically engineered viral sequences in heterologous, preferably rod-shaped coat, protein capsids. Since icosahedral viruses are limited in the amount of RNA they can carry, and rod-shaped viruses are expansible, this invention allows the size of recombinant virus RNA components to be increased (or decreased). Methods of making and using such recombinant viruses are also provided, specifically with respect to the transfection of plants to bring about genotypic and phenotypic changes.

11 Claims, 1 Drawing Sheet

PLASMID ENCODING HYBRID RNA VIRUS

This is a division, of application Ser. No. 08/473,617 filed Jun. 7, 1995 now U.S. Pat. No. 5,627,060, which is a divisional of Ser. No. 08/445,990, filed May 22, 1995, now U.S. Pat. No. 5,602,242 which is a continuation of Ser. No. 08/158,082, filed Nov. 23, 1993, abandoned, which is a continuation of Ser. No. 07/978,313, filed Nov. 17, 1992, abandoned, which is a continuation of Ser. No. 07/518,242, filed May 4, 1990, abandoned, which is a continuation of Ser. No. 07/012,253, filed Feb. 9, 1987, abandoned.

FIELD OF THE INVENTION

This invention relates to the use of RNA plant viruses for genetic engineering to transform plant cells and systemically infect plants, and in particular relates to packaging viral sequences in heterologous coat proteins.

BACKGROUND OF THE INVENTION

It has been recognized that RNA viruses are useful in the genetic engineering of plants, particularly +- strand messenger sense RNA viruses. See, e.g., U.S. patent application Ser. No. 580,445 and the continuation-in-part application thereof filed simultaneously herewith, and 709,181, incorporated herein by reference.

A problem with prior methods involving the use of RNA viruses for genetic engineering of plants, however, has been the fact that many plant viruses providing suitable sites for the insertion of RNA copies of foreign genes are encapsidated in their naturally infective state in spherical or icosahedral capsids which impose geometric constraints on the amount of genetic material which can be carried by these viruses.

Examples of such useful viruses are the tripartite viruses of Tricornaviridae, such as brome mosaic virus (BMV), and cowpea chlorotic mottle virus (CCMV), which are packaged in icosahedral capsids. The BMV RNA3 segment has been extensively studied as a carrier for heterologous RNA; however, observation of the structure of functional elements of this RNA segment indicate that the 3.2–3.3 kb size of the natural BMV RNA1 is probably near the maximum size which can be carried by the icosahedral BMV coat.

BMV RNA3 is around 2.1 kb in size, so only around 1 kb at most of foreign sequence could be added to a packagable RNA3 derivative without deletion of a portion of the natural BMV RNA3 sequence. Although in the case of BMV RNA3, which has been extensively studied, identification of sequences which are not required in cis for replication and gene expression opens the possibility of constructing variants with such deletions, it is highly desirable for increased freedom and flexibility in making more sophisticated virus derivatives to be able to add heterologous RNA sequences without being required to delete an equal amount of the original viral RNA. The possibility also exists for BMV and some other isometric viruses that lower as well as upper RNA size limits exist for viral RNA packaging (Ahlquist et-al. (1984) J. Mol. Biol. 172:369–383).

It would thus be desirable to encapsidate recombinant RNA viral sequences into a coat protein able to freely package pieces of RNA without upper or lower size constraints.

In contrast to the icosahedral viruses, a large class of plant viruses have elongated virions with the shape of rigid or flexuous rods. The tobacco mosaic virus is an example which has been extensively studied. See, e.g., M.H.V. Van Regenmortel (1981) "Tobamoviruses," in *Handbook of Plant Virus Infections and Comparative Diagnosis*, E. Kurstak (ed.), at 541–564; P. J. G. Butler (1984) "The Current Picture of the Structure and Assembly of Tobacco Mosaic Virus," J. Gen. Virol. 65:253–279; D. L. Beck, et al. (1985), "Synthesis of Full-length cDNA Clones of TMV," Phytopathology, 75:1334 (Abstract); and W. O. Dawson, et al. (1986) "cDNA Cloning of the Complete Genome of Tobacco Mosaic Virus and Production of Infectious Transcripts," Proc. Natl. Acad. Sci. U.S.A. 83:1832–1836.

The coat protein of such rod-shaped virions is encoded by an RNA gene. An assembly origin sequence is also necessary to initiate packaging. A cDNA clone containing the assembly origin of TMV Cowpea Strain (Cc) and coat protein gene has been isolated by T. Meshi, et al. (1981) "Nucleotide Sequence of a Cloned cDNA Copy of TMV (Cowpea Strain) RNA, Including the Assembly Origin, the Coat Protein Cistron, and the 3' Non-Coding Region," Mol. Gen. Genet. 184:20–25. In this particular TMV strain, the assembly origin sequences are within the coat protein gene; however, in other strains, the assembly origin and coat protein genes are separate.

The coat proteins of rod-shaped virions are assembled in a helical array, and encapsidate the RNA rod-shaped viral particle with RNA wound helically within the interior of the extendable particle. Thus, in order to increase the size range of genetically engineered RNA viral sequences, it is an object of this invention to provide a recombinant RNA sequence encapsidated in a rod-shaped coat.

In general, it would be desirable to package viral sequences in any heterologous coat protein capsid, for example when the desired host has established immunities against the natural coat protein of the viral sequence with which infection is desired. However, prior to this invention, no hybrid viruses combining functions (e.g., host specificity, infectivity, and the like) derived from more than one RNA virus had been constructed.

A viable recombinant was constructed at the cDNA level between poliovirus types 1 and 3 which are 70% homologous in RNA sequence (G. Stanway et al. (1986), "Construction of poliovirus intertypic recombinants by use of cDNA," J. Virol. 57:1187. This recombinant carried the 0.74 kb 5' untranslated sequence and first 11 polyprotein codons from type 3, with the remainder of the sequence from type 1. A second recombinant reported involved insertion of a portion of the VP1 capsid protein gene from type 3 into a type 1 context, but this was non-viable, indicating problems in combining non-homologous functional regions.

An additional example of recombination between divergent Picornavirus genomes was the construction of a recombination between poliovirus type 1 and coxsackie B3 virus (B. L. Semler et al. (1986), "A chimeric plasmid from cDNA clones of poliovirus and coxsackie virus that is temperature-sensitive," Proc. Natl. Acad. Sci. USA 83:1777). In this case a 0.4 kb segment of the coxsackie B3 5' noncoding region was inserted in a poliovirus context, replacing a segment with which it had 70% homology. The resulting recombinant virus was viable but showed a temperature-sensitive replication phenotype.

In none of these reported attempts to produce recombinant viruses was a viable hybrid virus produced in which a substitute segment had less than 70% homology with the segment it replaced, and in no case were separate functions from two or more different viruses successfully recombined. Nor has the artificial construction of a hybrid RNA plant virus from two distinct viral types been reported.

Unencapsidated derivatives of rod-shaped viruses have been recently used as vectors to carry a foreign gene in recombinant RNA (Takamatsu, N. et al., "TMV-RNA mediated foreign gene expression in tobacco plants," In press), and recombinant RNA sequences have been encapsidated in a rod-shaped coat in vitro (Sleat, D. E. et al., "Packaging of Recombinant RNA Molecules into Pseudovirus Particles Directed by the Origin-of-Assembly Sequence from Tobacco Mosaic Virus RNA," In press). However, the in vivo packaging of a recombinant viral RNA in a capsid foreign to the infective viral sequences has not been previously reported.

SUMMARY OF THE INVENTION

RNA viruses make useful vectors for genetic engineering of plants and other higher organisms to confer useful traits such as herbicide, disease and pest resistance, however existing systems are not as flexible as is desired. Encapsidation of an RNA viral sequence appears to be required for its significant and reliable spread through the host system. Uncoated RNA viruses, for example, can infect single cells and protoplasts, and in the case of some single component RNA viruses, can spread erratically to sites distant from the original inoculation site. However, efficient transmission throughout the plant from a single site of infection or transfection, particularly for the many multicomponent plant RNA viruses, requires encapsidation in a viral coat. This invention provides methods for creating hybrid viruses in which infective viral sequences are packaged in heterologous coat protein capsids. Encapsidated hybrid virions are also provided, as well as hybrid viral RNA sequences capable of encapsidation in vitro or in vivo.

As used herein, the term "hybrid RNA virus" refers to recombinant viruses in which functional sequences from two or more different viruses are combined to form a viable organism. Specifically, the hybrid RNA viruses of this invention are RNA sequences comprising infectious viral sequences derived from one RNA virus, and an origin of assembly and coat protein gene derived from another virus (or other viruses). The term "hybrid RNA virion" refers to the encapsidated form of such viruses.

Many useful RNA viruses are encapsidated in icosahedral coats which limits the size of genes that can be added. A method of encapsidating RNA viral sequences in rod-shaped coat protein capsids is therefore provided. These coat protein capsids are expansible to accommodate large-sized RNA fragments up to at least the 6.4 kb size of the tobacco mosaic virus. RNA fragments as large as desired may be encapsidated in rod-shaped particles so long as the particles are not so large as to be substantially broken by normal physical manipulations.

A recombinant viral RNA sequence is provided in which original viral sequences from a virus normally encapsidated in one type of coat protein are encapsidated in a different type. Preferably an infectious virus normally encapsidated in an icosahedral capsid or otherwise not normally encapsidated in a rod-shaped capsid are combined with genes and assembly origins for the production of a rod-shaped capsid, thus enabling encapsidation of the original viral sequences in a rod-shaped capsid. The original viral sequences preferably are modified to contain desirable foreign genes.

An original viral RNA sequence suitable for combining with heterologous coat protein genes and assembly origins is a sequence derived from or corresponding to that of an RNA virus. Examples of such viruses are plus strand viruses such as BMV, Tricornaviridae in general, and many others, as known to the art. Further useful virus sequences are those derived from or corresponding to reverse-transcribed viral or transposon RNA, viroids and virus satellites.

Such viral sequences must as a minimum have the functions of replicability in the host and ability to infect the host. Determinants of such functions may be required in cis or in other cases may be suppliable in trans. An example of a replication requirement satisfiable in trans is the need for the presence of the proteins encoded by BMV RNA's 1 and 2 in order to allow BMV RNA3 to replicate in a host. In contrast, certain replication signals must be present in cis (i.e, directly linked to RNA3 derivatives) to allow replication of RNA3 derivatives by the machinery induced in the infected cell by RNA's 1 and 2.

It is also desirable that such original viral sequences have suitable sites for the addition of foreign or heterologous genes. The terms "foreign" and "heterologous" in reference to genes and sequences mean genes or sequences not encoded in the original virus in nature. Such foreign genes or sequences may be inserted in any location not giving rise to interference with the necessary functions of the original viral sequences, i.e., the ability to replicate and infect a host. In reference to expression in a host, a "heterologous" gene is one which is not naturally present in the location in the host in which it has been placed.

Similarly, it is desirable that the placement of the heterologous coat protein genes and assembly origins not interfere with such necessary functions of the original viral sequences.

Coat protein sequences from flexible or rigid rod-shaped RNA viruses are especially useful in this invention, in combination with an assembly origin capable of regulating the coat protein sequences. Generally, as is recognized in the art, assembly origins are specific to their coat protein genes, so it is preferred that the coat protein genes and assembly origins are derived from the same organism. Coat protein genes containing their assembly origins within the gene, e.g. TMV Cowpea (Cc) strain genes, are particularly preferred.

The foreign RNA sequences added to the original viral RNA may be or encode functional RNA's, and the host organism may be transfected and transformed genotypically or phenotypically. A functional RNA is one which provides any function which is appropriate and known to be provided by an RNA segment. Such functions include, but are not limited to coding functions in which the RNA acts as a messenger RNA encoding a sequence which, translated by the host cell, results in synthesis of a peptide or protein having useful or desired properties. Such proteins are termed "functional proteins" herein. The RNA segment may also be structural, as for example in ribosomal RNA; it may be regulatory, as for example with small nuclear RNA's or anti-sense RNA, or it may be catalytic. Anti-sense RNA is useful to inhibit the function of complementary RNA in the target cell.

As will be appreciated by those skilled in the art, if the inserted RNA sequence is in the form of messenger-sense RNA comprising genes to be directly translated by the transformed cell, the genes must be free of intervening, non-translated sequences, such as introns. On the other hand, inserted genes need not be naturally occurring genes, but may be modified, composites of more than one coding segments, or encode more than one protein. The RNA may also be modified by combining insertions and deletions in order to control the total length or other properties of the modified RNA molecule.

The inserted foreign RNA sequences may be non-viral or viral in origin, and may correspond either to RNA or DNA in nature. They may be prokaryotic or eukaryotic in origin, so long as they are in a form which can be directly translated by the translation machinery of the recipient cell or otherwise recognized and utilized for their functional, structural or regulatory functions.

As discussed above, "expression" of the foreign RNA sequences may involve the production of functional RNA's or functional proteins. This expression may be at any useful level, and as will be appreciated by those skilled in the art, suitable regulatory elements may be necessary depending on the product desired and the host used. Providing such regulatory elements is a matter of ordinary skill in the art.

The natural TMV RNA is about 6.4 kb in length Rod-shaped capsids of this invention, however, may be as long or as short as required. As the maximum size the icosahedral capsid of BMV is believed capable of encapsidating is about 3.2 kb, it can be seen that the use of a rod-shaped coat considerably expands the size range of engineered viral sequences that can be made competent by encapsidation for systemic spread in hosts previously accessible only to icosahedrally encapsidated viruses.

As discussed below, insertion of foreign RNA sequences is preferably done through reverse transcription of all sequences involved into corresponding cDNA, or in the case of foreign sequences originally derived from DNA, original DNA sequences can be used. Any suitable vector may be used to provide a basis for carrying out such genetic engineering, all as will be evident to those skilled in the art. Preferred plasmids are discussed in the Example hereof. Techniques for constructing desired DNA sequences or combinations of DNA fragments are well known to the art, using appropriate restriction enzymes, ligation techniques and oligonucleotide-directed alterations available for constructing combinations of fragments containing the desired functions. Techniques for testing such constructions to assure their operativeness are also well known and will not be discussed in detail herein.

Similarly, any art-known bacterial host for vectors containing the DNA sequences of this invention may be utilized in conducting the genetic engineering and/or obtaining RNA transcripts of the DNA sequences in vivo. RNA transcripts may also be produced in vitro, for example by the methods of U.S. Ser. No. 580,445 and the continuation-in-part application thereof.

Any plant may be infected with an RNA sequence of this invention, as will be evident to those skilled in the art, by providing appropriate host specificity and replication functions. With appropriate constructions, other eukaryotic organisms may also be infected, as may single cells and tissue cultures. This invention is not limited to any given class of host or type of RNA virus. The general utility of providing a heterologous protective coat or encapsidation, especially one allowing size expansion to a viral sequence, will be recognized by those skilled in the art as an improvement in any process involving the use of viruses which can be improved by added RNA sequences.

The term "systemic infection" means infection spread through the system of the host organism to involve more than the cells at the site of original inoculation. The entire host organism need not be infected; single organs or even parts of organs are sufficient, depending on the purpose of the infection.

The term "transfected" as applied to the host organism means incorporation of the viral sequences of this invention into the cells of the organism in such as a way to be replicated therein. To be transfected, the organism need not be systemically infected, but is preferably systemically infected.

Methods for initiating infection of the host organism are well known to the art, and any suitable method may be used. A preferred method for the infection of plants is to contact the wounded plant with a solution containing the virus or viral RNA so as to cause the virus to replicate in, or infect the plant.

DETAILED DESCRIPTION OF THE PREFERRED EMBODIMENTS

Figure 1:
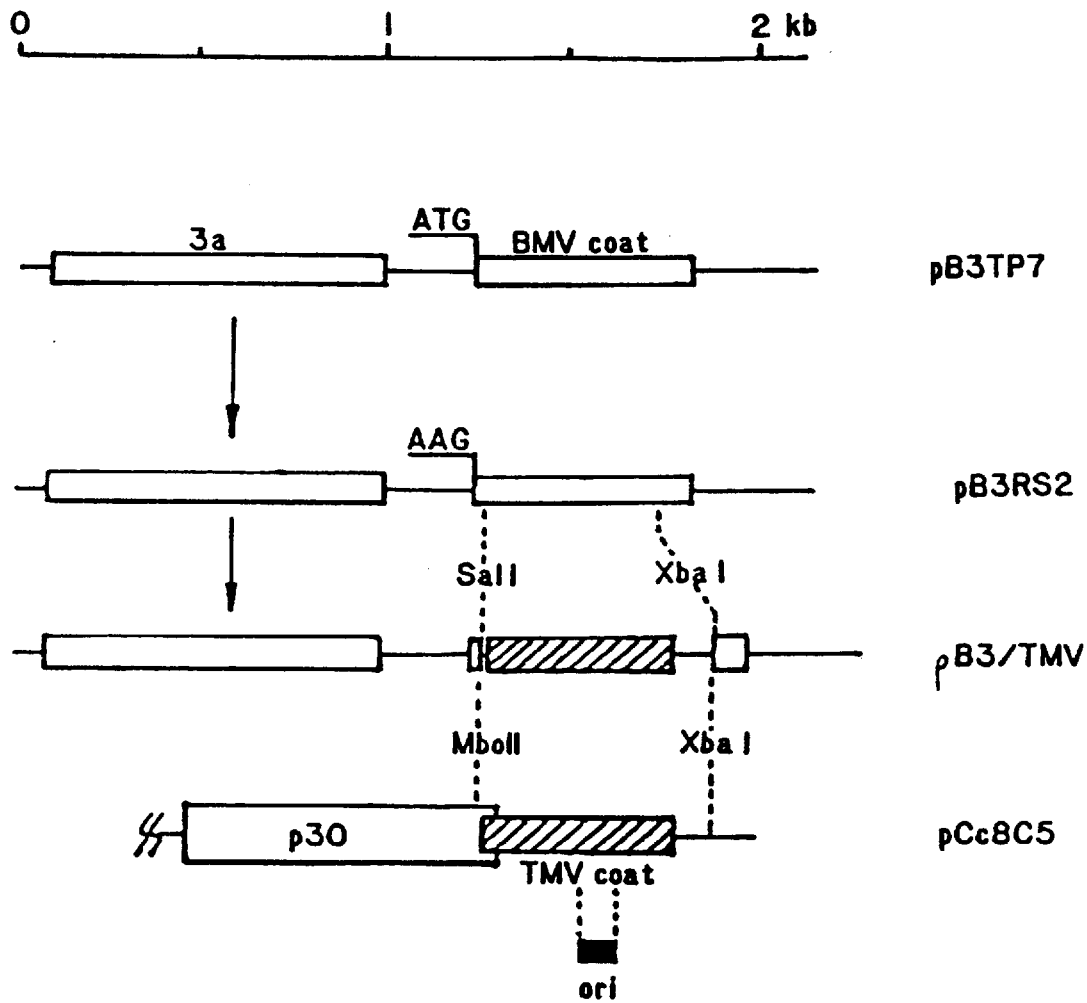
FIG. 1 shows a schematic diagram of the viral cDNA regions of plasmids pB3TP7 containing BMV RNA3, pB3RS2 having the coat protein start codon modified from ATG to AAG, pB3/TMV having the TMV coat protein and assembly origin substituted for the BMV RNA3 coat protein, and pCc8C5 containing the TMV coat protein and assembly origin, showing construction of pB3/TMV.

In a preferred embodiment of this invention, an RNA segment of an icosahedral virus, preferably a tripartite virus, and more preferably BMV, is packaged in a cylindrical capsid, preferably of TMV, and more preferably of TMV Cowpea strain (Cc) coat protein. Preferably, the packaged sequence is also modified to contain a heterologous gene.

The genome of BMV is divided among messenger sense RNA's 1, 2 and 3 of 3.2, 2.9 and 2.1 kb respectively. cDNA copies of these RNA's have been cloned into the universal transcription vector pPM1 which was deposited with the American Type Culture Collection, Rockville, Md., on Mar. 7, 1984, as No. 40172. The clones, containing RNA's 1, 2 and 3, respectively are designated pB1PM18, pB2PM25 and pB3PM1, and were deposited with the ATCC on the same date as Nos. 40171, 40170 and 40169 respectively. In order for cells to be infected with BMV RNA3, the proteins encoded by BMV RNA's 1 and 2 must be present. In the preferred embodiment these three BMV RNA's are separately encapsidated in the rod-shaped virus coat protein.

In the preferred embodiment, BMV RNA's 1, 2 and 3 each contain an appropriate assembly origin, but only the BMV RNA3 sequence contains an added coat protein although any of the sequences may be modified to contain additional RNA sequences such as sequences encoding functional protein or functional RNA's. Methods of modifying DNA sequences to insert heterologous or foreign sequences are well known to the art. Generally the viral RNA sequence is converted to a full-length cDNA transcript and cloned into a vector, then modified by inserting a foreign DNA segment in a region able to tolerate such insertion without disrupting RNA replication or disturbing infectivity.

It is necessary that the viral RNA being packaged have the gene for its own coat protein deleted or inactivated so as to avoid interference with the added coat protein gene. Means for inactivating viral coat protein genes are well known to the art. See, e.g. Ahlquist et al. (1981) "Complete Nucleotide Sequence of Brome Mosaic Virus RNA3," J. Mol. Biol. 153:23–38. A preferred method for inactivating the gene is simply by deletion of the gene or substantial portions thereof. Other methods include point mutation or insertional inactivation.

In order to ensure translational fidelity of the heterologous coat protein gene, it may also be necessary to modify the the translation initiation ATG codon for the original coat protein if this is not deleted, and this may be accomplished by means known to the art, such as oligonucleotide-directed substitution. If the coat protein sequence to be added has its own translational start codon, deletion or inactivation of the start codon for the original protein is necessary; alternatively, however, it may be retained and used to initiate translation of the added coat protein sequence, provided that any amino acid sequence changes introduced thereby do not interfere with RNA packaging and capsid formation.

Many RNA viruses producing rod-shaped virion particles are known to the art (See, e.g., *Plant Virology* (2nd ed.), R. E. F. Matthews (1981) Academic Press, New York, and "4th Report of the International Committee on Taxomony of Viruses", (1982) Intervirology 17:1–199. Useful coat protein and origin of assembly sequences may be isolated and reverse transcribed from such viruses by means known to the art without undue experimentation. Preferred sequences are TMV sequences, and most preferred are coat protein genes incorporating their own assembly origins such as the coat protein gene of TMV Cowpea (Cc) strain. Plasmid pCc8C5 of Meshi et al., supra, contains cDNA corresponding to such sequences, and was obtained from Meshi et al. for the work discussed here. The wide availability of this strain and the fact that the sequences of the coat protein gene and origin of assembly have been published (Meshi et al., supra) makes the reconstruction of this plasmid and/or said sequences a matter of ordinary skill in the art.

Through standard cloning techniques, the coat protein gene and assembly origin sequences of rod-shaped virions are ligated into the viral sequences to be packaged, preferably at the site where the original coat protein gene for the virus was removed, but in any event at a site which does not interfere with the ability of the virus to replicate and infect its hosts.

Translational expression of the inserted new coat protein gene may be provided by known means. In the example, the TMV coat protein gene was inserted immediately downstream of the initiation site for subgenomic BMV RNA4, leading to BMV-directed synthesis of a subgenomic mRNA for TMV coat protein. The TMV gene is thus said to be placed downstream of a "subgenomic promoter."

The foreign genes for which expression in the host plant is desired may be inserted at any convenient location in the genome of the original virus which does not interfere with the ability of the virus to replicate and infect the host. Preferably the foreign genes are inserted immediately upstream from the coat protein and its subgenomic promoter. A copy of the subgenomic promoter normally regulating coat protein in the original virus may also be placed upstream of such foreign genes to allow for their translational expression.

RNA transcripts are prepared, in vivo, such as in bacterial hosts, or in vitro, all as known to the art, and used to inoculate an appropriate plant host or plant tissue. The RNA can be used in encapsidated form or in solution, since encapsidation will occur within the host organism.

As will be understood by those skilled in the art, a given virus may require special conditions for optimal infectivity and replication, including the presence of genes acting in cis or in trans, all of which should be present when infecting the plant or plant tissue. For example, for infectivity of BMV RNA3, the presence of BMV RNA1 and 2 is necessary. Moreover, infection by a virus having the necessary host-specificity genes for a given host can in some circumstances allow infection of the host by a second virus which does not normally affect that host, e.g. mixed TMV and BMV viruses will infect both barley and tobacco even though BMV alone does not infect tobacco and TMV alone does not infect barley. Hamilton and Nichols (1977) Phytopathology, 67:484–489. It is not necessary that all the required genes be identified and mapped if the entire original virus providing the necessary genes is used.

Suitable genes which may be inserted into the original viral segment for expression in the host plant include the CAT (chloramphenicol transferase) gene, pest resistance genes, e.g. *Bacillus thuringiensis* insecticidal protein genes, pathogen resistance, herbicide tolerance or resistance, modified growth habit and new metabolic pathway genes, and genes for production of commercially useful peptides or pharmaceuticals in plants or other host organisms. In general, any heterologous gene whose expression product is functional within the plant cell can be inserted into the viral expression system described herein.

Plants may be transfected both under field and greenhouse conditions. The modifications can be applied at any time during the growth cycle, depending on the need for the trait. For example, resistance to a pest could be conferred only if the crop were at risk for the pest, and at the time when the crop was most likely to be affected by the pest. Other traits can be used to enhance secondary properties, for example to increase the protein content of post-harvest forage. Any plant variety susceptible to infection by an RNA virus can be phenotypically transformed. The choice of virus and the details of modification will be matters of choice depending on parameters known and understood by those of ordinary skill in the art.

Other uses for cells and organisms phenotypically or genotypically modified by means of a modified RNA derived from an RNA virus will be readily apparent to those skilled in the art, given a wide range of RNA viruses to modify and a wide range of susceptible host cell types. Other uses for transfected animal cells, bacterial cells and the like can be readily envisioned For example, animal cells susceptible to infection by the alphaviruses, which share homologous nonstructural proteins and many features of viral replication with BMV, may be infected in cell culture with a modified alphavirus carrying a desired gene and thereby caused to express large quantities of a desired protein within a short time. The encapsidated RNA viruses of this invention are especially useful when it is necessary to subject the virus to harsh conditions, due either to environmental conditions or host defenses, which would inactivate the uncoated virus.

The method of making and using genetically engineered viruses is described herein with particular reference to BMV RNA's, but the ordinarily skilled artisan will be able to apply the principles described, using known techniques, to other viral RNA's.

EXAMPLE

The following discussion describes the insertion of a TMV coat protein gene and assembly origin in BMV RNA3, expression of the inserted gene, and in vivo packaging of the hybrid RNA in rod-shaped particles.

As shown in FIG. 1, plasmid pB3TP7 contains the full-length cDNA copy of BMV RNA3 from plasmid pB3PM1 fused to a promoter for bacteriophage T7 RNA polymerase, allowing biologically active RNA3 transcripts to be produced in vitro. The initiating ATG codon of the BMV coat protein in this plasmid was modified by oligonucleotide-directed substitution (Zoller and Smith (1982) Nucl. Acids Res. 10:6487–6500; Kunkel (1985) Proc. Natl. Acad. Sci. 82:488–492) to an AAG codon to generate plasmid pB3RS2.

Plasmid pCc8C5 contains a partial cDNA copy of the RNA of the cowpea (Cc) strain of tobacco mosaic virus (Meshi et al, supra). Using standard methods (Maniatis et al. (1982) Molecular Cloning, CSH Laboratory), the approximately 0.5 kb SalI-XbaI fragment of PB3RS2 interior to the BMV coat gene was then replaced by the approximately 0.6 kb MboII-XbaI fragment of PCc8C5, which contains the entire coat protein gene of TMV Cc, including sequences believed to represent the encapsidation origin of the RNA (Meshi, et al., supra). The SalI and MboII restriction fragment ends we re both repaired to blunt ends with T4 DNA polymerase prior to ligation. The resulting plasmid will be referred to as pB3/TMV.

Transcripts from EcoRI-linearized pB3/TMV, including the complete BMV RNA3 and TMV sequences contained in that plasmid were inoculated onto barley protoplasts along with infectious transcripts of BMV RNA1 and RNA2 cDNA clones (French, et al. (1986) Science 231:1294–1297.) The pB3/TMV RNA's were replicated in such infections and gave rise to a subgenomic RNA of the size expected for a mRNA initiated at the normal BMV RNA3 subgenomic initiation site and containing all sequences between that point and the 3' end of the BMV RNA sequence, including the TMV Cc sequence insertion.

RNA samples were derived from protoplasts inoculated with transcripts of wild type cDNA copies of BMV RNA's 1 and 2 and either no additional transcript (−) or transcripts of either wild type BMV RNA3 cDNA or pB3/TMV. Fluorographs of 3H-uridine labelled RNA's separated on a 1% (w/v) agarose gel after extraction from protoplast samples variously inoculated and incubated for 20 hours in light at 24 degrees C showed the presence of all these RNA's.

It When freeze/thaw lysates of barley protoplasts infected with transcripts of BMV RNA1, RNA 2 and pB3/TMV were sampled by serologically-specific electron microscopy (K. S. Derrick and R. H. Brlansky (1976) Phytopathology 66:815–820) using anti-TMV virion antibody, rod shaped particles were consistently visualized in repeated experiments. These particles had several features highly characteristic of normal TMV virion particles, including an approximately 20 nm diameter and a central uranyl acetate-staining channel. The particles were predominantly around 110 nm in length, while the longest particles visualized in the same way from protoplasts infected with TMV Cc virion RNA were around 310 nm in length.

Assuming a length of 6.4 kb for TMV RNA (Goelet et al. (1982) Proc. Natl. Acad. Sci. 82:488–492), and a constant ratio of RNA to particle length (Butler, supra), these results imply that the major particle form from pB3/TMV infected protoplasts contains an approximately 2.3 kb RNA, and that the length of the pB3/TMV RNA is approximately 2.2 kb. A small fraction of shorter particles was also seen in the pB3/TMV derived preparations, and a larger fraction and a broader length distribution of particles shorter than 310 nm was also seen from TMV Cc-infected preparations. Such smaller particles may arise from breakage of larger particles or from encapsidation of subgenomic RNA's.

The foregoing example is provided by way of illustration and not by way of limitation of the invention.

We claim:

1. A plasmid containing cDNA complementary to the RNA sequence of a hybrid RNA molecule capable of infection of and replication in a host cell, said hybrid RNA molecule comprising a first RNA sequence derived from a first virus and a second RNA sequence from a second virus having a morphologically-different type of coat protein, said second RNA sequence comprising an origin of assembly and encoding a coat protein heterologus to said first virus, wherein the coat protein gene of said first virus is deleted from or inactivated in said first RNA sequence and said second RNA sequence is substituted therefor to produce a hybrid molecule capable of expressing the coat protein gene of said second virus.

2. The plasmid of claim 1, wherein said RNA molecule is capable of encapsidation in vivo.

3. The plasmid of claim 1, wherein said RNA molecule further comprises a sequence heterologous to said first virus which encodes a functional protein.

4. The plasmid of claim 1, wherein said first virus is an icosahedral virus.

5. The plasmid of claim 1, wherein said first virus is a rod-shaped virus.

6. The plasmid of claim 1, wherein said RNA molecule has a length greater than about 3.2 kb.

7. The plasmid of claim 1, wherein the origin of assembly and coat protein gene are derived from TMV.

8. The plasmid of claim 1, wherein said RNA sequence from said first virus is BMV RNA3.

9. The plasmid of claim 1, wherein said first virus is a plant virus.

10. A plasmid containing cDNA, complementary to the RNA sequence of a hybrid RNA molecule capable of infection of and replication in a host cell, said hybrid RNA molecule comprising an RNA segment derived from a first non-rod-shaped virus and an RNA sequence from a second rod-shaped virus, said second virus RNA sequence encoding an origin of assembly and coat protein heterologous to said first virus, wherein said second virus RNA sequence is placed in a region of the RNA segment of said first virus to produce a hybrid RNA molecule, wherein said region is able to tolerate such sequence without disrupting RNA replication of or infection by said hybrid RNA molecule.

11. A plasmid containing cDNA complementary to the RNA sequence of a hybrid RNA molecule capable of infection of and replication in a host cell, said hybrid RNA molecule comprising a BMV RNA3 sequence and an RNA sequence comprising an origin of assembly and encoding a coat protein derived from TMV, wherein the BMV coat protein gene is deleted from or inactivated in said BMV RNA3 sequence and said TMV RNA sequence us substituted therefor to produce a hybrid RNA molecule capable of expressing the coat protein encoded by said TMV RNA sequence.

* * * * *

UNITED STATES PATENT AND TRADEMARK OFFICE
CERTIFICATE OF CORRECTION

PATENT NO. : 5,804,439

DATED : September 8, 1998

INVENTOR(S) : Paul G. Ahlquist, Roy C. French, and Robert F. Sacher

It is certified that error appears in the above-identified patent and that said Letters Patent is hereby corrected as shown below:

Column 1, line 58: "et-al." should read --et al. --.

Column 5, line 12: "length Rod-" should read --length. Rod- --.

Column 9, line 29: "It When freeze/thaw" should read --When freeze/thaw.--.

Column 10, line 9: "heterologus" should read --heterologous--.

Column 10, line 13: "hybrid molecule" should read --hybrid RNA molecule--.

Signed and Sealed this

Twelfth Day of January, 1999

Attest:

Attesting Officer

*Acting Commissioner of Patents and Trademarks*